United States Patent [19]

St. Clair et al.

[11] Patent Number: 5,302,692
[45] Date of Patent: Apr. 12, 1994

[54] POLYIMIDES CONTAINING THE PENTAFLUOROSULFANYLBENZENE MOIETY

[75] Inventors: Anna K. St. Clair; Terry L. St. Clair, both of Poquoson, Va.

[73] Assignee: The United States of America as represented by the Administrator of the National Aeronautics and Space Adminstration, Washington, D.C.

[21] Appl. No.: 77,132

[22] Filed: May 27, 1993

Related U.S. Application Data

[63] Continuation-in-part of Ser. No. 755,207, Sep. 5, 1991, Pat. No. 5,220,070.

[51] Int. Cl.$^5$ .................. C08G 73/10; C08G 69/26
[52] U.S. Cl. ................... 528/353; 528/125; 528/128; 528/170; 528/172; 528/173; 528/174; 528/176; 528/183; 528/188; 528/220; 528/229; 528/350; 528/352; 528/373; 428/473.5
[58] Field of Search ............ 528/125, 128, 170, 172, 528/73, 174, 176, 183, 188, 220, 229, 350, 352, 353, 373; 428/473.5

[56] References Cited

U.S. PATENT DOCUMENTS

| | | | |
|---|---|---|---|
| 4,975,521 | 12/1990 | Fjare et al. | 528/353 |
| 4,978,573 | 12/1990 | Kohn | 528/353 |
| 5,061,783 | 10/1991 | St. Clair | 528/353 |
| 5,093,453 | 3/1992 | St. Clair et al. | 528/353 |
| 5,112,941 | 5/1992 | Kasai et al. | 528/353 |
| 5,116,939 | 5/1992 | Fletcher et al. | 528/353 |
| 5,218,077 | 6/1993 | St. Clair et al. | 528/353 |
| 5,225,517 | 7/1993 | Faron | 528/353 |
| 5,232,472 | 8/1993 | Simmons et al. | 528/353 |

Primary Examiner—Harold D. Anderson
Assistant Examiner—P. Hampton-Hightower
Attorney, Agent, or Firm—George F. Helfrich

[57] ABSTRACT

The diamine, 1,3-diamino-5-pentafluorosulfanylbenzene (DASP), was reacted with various dianhydrides to form polyimides containing an $SF_5$ moiety. These polyimides exhibit high glass transition temperatures, high density, low solubility, and low dielectric properties. These polymers were used to prepare semi-permeable membranes, wire coatings, and films and are useful for electronic, space and piezoelectric applications.

11 Claims, No Drawings

POLYIMIDES CONTAINING THE PENTAFLUOROSULFANYLBENZENE MOIETY

ORIGIN OF THE INVENTION

The invention described herein was jointly made by employees of the United States Government and may be manufactured and used by or for the Government for governmental purposes without the payment of any royalties thereon or therefor.

CROSS-REFERENCE

This application is a continuation-in-part of copending patent application Ser. No. 07/755,207 filed Sep. 5, 1991 now U.S. Pat. No. 5,220,070.

BACKGROUND OF THE INVENTION

1. Field of the Invention

The present invention relates to polyimides. In particular, it relates to polyimides containing the pentafluorosulfanylbenzene moiety.

2. Description of Related Art

Polyimides containing a trifluoromethyl moiety have been prepared from the diamine, 3,5-diaminobenzotrifluoride (DABTF), which contains one symmetrically substituted, polar $CF_3$ group. These polymers are more soluble, have greater optical transparency and lower dielectric constants than state-of-the-art polyimides. The glass transition temperatures (Tg) of these polymers are similar to those prepared from m-phenylenediamine and they also exhibit high thermooxidative stability. These polymers are easily processible due to their enhanced solubility and are useful in any electronic and aerospace applications where high thermooxidative stability, optical transparency and excellent dielectric characteristics are needed.

Despite these properties, there is a desire to have a polymer which not only has low dielectric properties but a higher Tg, higher density, and lower solubility than those of the $CF_3$ containing polyimides. This combination of properties would allow the polymer to be used at higher temperatures, harsher environments, and in applications where polymer to substrate compatibility is important such as piezoelectric applications.

An object of the present invention is to prepare polyimide polymers containing a pentafluorosulfanylbenzene moiety.

Another object of the present invention is to prepare polyimide polymers which exhibit high Tg, high density, low solubility, and low dielectric properties.

SUMMARY OF THE INVENTION

The diamine, 1,3-diamino-5-pentafluorosulfanylbenzene (DASP), was prepared and has the structural formula:

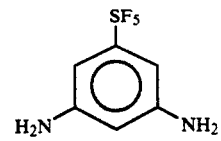

Polyimides having the structural formula:

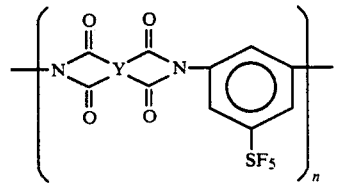

where Y is any aromatic moiety and n=10-100, were prepared from the DASP. The synthesis of these polymers involved dissolving the DASP in a solvent, such as N,N-dimethylacetamide, adding a dianhydride, and allowing the materials to react. Examples of the dianhydrides used in the present invention are listed below.

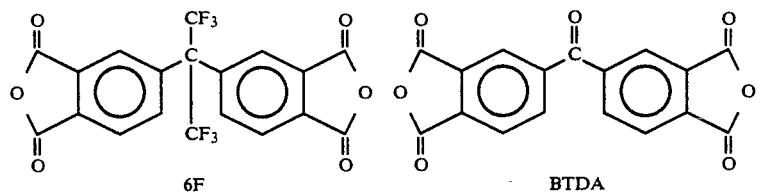

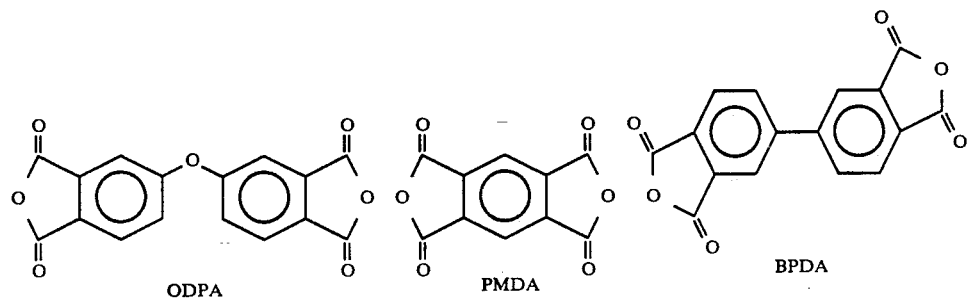

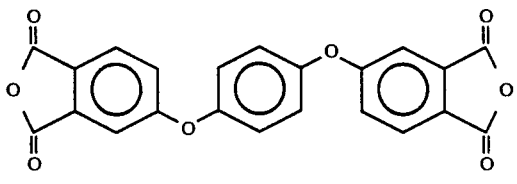

HQDEA

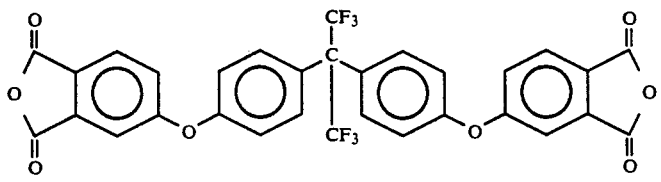

BFDA

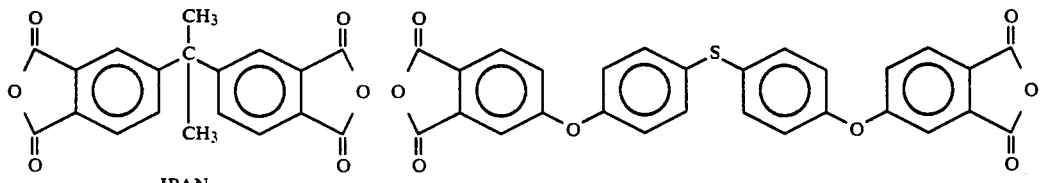

IPAN                                    BDSDA

The resulting polymers exhibited higher glass transition temperatures (Tgs), higher densities, and lower solubilities than the CF$_3$ containing polyimides and the dielectric properties were similar to those polyimides which contain the CF$_3$ moiety. The SF$_5$ containing polyimides are useful for electronic, space, and piezoelectric applications.

DESCRIPTION OF THE PREFERRED EMBODIMENTS

In the present invention, a series of aromatic polyimides containing a pentafluorosulfanylbenzene moiety was prepared. These polymers were characterized for their glass transition temperature (Tg), solubility, density, dielectric constant, thermal stability, and film appearance.

The polymers prepared from the diamine, 1,3-diamino-5-pentafluorosulfanylbenzene (DASP) had improved properties over those polymers which were CF$_3$ substituted. The Tgs for these polymers were higher than the CF$_3$ substituted polymers. Table 1 shows a comparison of the glass transition temperatures for the polymers containing SF$_5$ moieties as compared with those containing CF$_3$ groups.

TABLE 1

Glass Transition Temperatures of CF$_3$ and SF$_5$ Substituted Polyimides

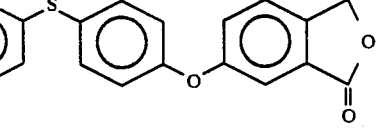

| Dianhydride | CF$_3$ (H$_2$N-—NH$_2$) | SF$_5$ (H$_2$N-—NH$_2$) |
|---|---|---|
| BTDA  | 294 | 308 |
| BPDA  | 329 | 344 |
| OPDA  | 274 | 287 |
| BDSDA | 218 | 235 |
| BFDA  | 231 | 243 |
| IPAN  | 287 | 300 |
| 6FDA  | 297 | 305 |
| HQDEA | N/A | 263 |

N/A - not available

The data show that in all cases, the Tgs for the SF$_5$ containing polyimides are consistently higher than the CF$_3$ substituted polyimides, enabling a higher use temperature for the SF$_5$ polyimides.

In addition, the solubility of these polymers were lower and the density was higher than their CF$_3$ counterparts. Table 2 lists the densities of the SF$_5$ polymers as compared to those containing CF$_3$.

TABLE 2

Densities of CF$_3$ and SF$_5$ Containing Polyimides

| Dianhydride | CF$_3$ | SF$_5$ |
|---|---|---|
| 6FDA  | 1.512 | 1.559 |
| BFDA  | 1.457 | 1.503 |
| BPDA  | 1.454 | 1.529 |
| IPAN  | 1.350 | 1.436 |

The higher densities of the SF$_5$ containing polyimides allows them to be useful in piezoelectric applications in order to match mechanical coupling into media such as water and as a matrix for piezoelectric ceramic particles where CF$_3$ substituted polyimides are not used.

The dielectric constants for the SF$_5$ containing polyimides were comparable to those of the CF$_3$ substituted polyimides.

Several articles were prepared from these polymers. These articles include: semi-permeable membranes, wire coatings, and films.

The following examples are merely illustrative of the invention and are intended to enable those skilled in the art to practice the invention in all of the embodiments flowing therefrom, and do not in any way limit the scope of the invention as defined in the claims.

EXAMPLE 1

A 1000 ml capacity stainless steel reactor, tested at 60 p.s.i. pressure and pre-treated with fluorine, was charged with 165 g of silver fluoride (AgF$_2$), 30 g of bis(3,5-dinitrophenyl)disulfide, ten copper sheets (0.1×15×60 mm), and then an additional 150 g of AgF$_2$. The reactor was evacuated on a vacuum line, and 200 ml of 1,1,2-trichlorotrifluoroethane was added while maintaining the reactor at −80° C. The reactor was shaken for 5 minutes, warmed to room temperature, and then placed in an oil bath and heated to 60° C.

After two hours at 60° C., the temperature of the oil bath was gradually increased over 30 minutes to 130° C. During a two hour period at 130° C., the reactor was shaken at 30 minute intervals for 5 minutes. The reactor was then cooled to room temperature, and the 1,1,2-trichlorotrifluoroethane was removed under vacuum. The product was extracted from the reaction mixture three times with 150 ml portions of carbon tetrachloride (CCl$_4$) and two times with 150 ml portions of trichloromethane (CHCl$_3$).

The extracts were combined and the CCl$_4$ and CHCl$_3$ were distilled off under vacuum. The resulting residue, a yellow oil (25.6 g), was further purified by HPLC using Lichroprep RP-18 ® packing, which is commercially available, and a water-methanol (1:1) mixture as eluent. The volume of the fractions containing 1,3-dinitro-5-pentafluorosulfanylbenzene was reduced in half whereupon the product precipitated. The solid product (3.1 g, 7.0% yield) was filtered and dried. The structure of the compound was confirmed by $^1$H, $^{19}$F, and $^{13}$C NMR spectroscopy, mass spectrometry, and elemental analysis.

1,3-(NO$_2$)$_2$-5-SF$_5$-C$_6$H$_3$: mp 73°–75° C.; $^1$H NMR δ 9.25 (t, J=1.7 Hz, 1H), 8.96 (d, J=1.7 Hz, 2H); $^{19}$F NMR (ab$_4$ pattern) δ$_a$ 77.6 (m), δ$_b$ 62.7 (d of m) (J$_{AB}$=152.4 Hz); $^{13}$C NMR δ C-1=C-3 148.5, C-2 121.7, C-4=C-6 126.7 (quintet, J$_{SF4-C}$=4.8 Hz); C-5 154.6 (quintet, J$_{SF4-C}$=21.5 Hz). Mass Spectrum (70 eV) m/e (rel. intensity) 294 M+ (100.0), 275 [M-F]+ (20.9), 248 [M-NO$_2$]+ (28.4), 218 [M-N$_2$O$_3$]+ (34.3), 202 [M-N$_2$O$_4$]+ (13.9), 201 (94.5), 167 [M-SF$_5$]+ (10.7), 127 SF$_5$+ (3.8).

Anal.—Calcd. for C$_6$H$_3$F$_5$N$_2$O$_4$S (294.2): C, 24.50; H, 1.03; N, 9.52; S, 10.90.

Found: C, 24.75; H, 1.05; N, 9.53; S, 10.64.

The 1,3-Dinitro-5-pentafluorosulfanylbenzene (4.43 g, 15.1 mmol) was combined with 100 ml absolute ethanol, 10 ml chloroform, 2.65 g of 41.59% hydrochloric acid (HCl) in ethanol, and 2.65 g platinum oxide (Pt$_2$O) and were placed in a 500 ml pressure bottle for use on a Parr hydrogenation apparatus. The system was flushed, pressurized to 100 p.s.i. with hydrogen, and shaken. Within 1 hour the theoretical amount of hydrogen was absorbed. After filtration through Celite ®, which is commercially available from Johns-Manville Products Corporation, on a Büchner funnel, the volatile materials were distilled off at room temperature. The resulting solid (crude amine hydrochloride, 5.43 g) was then neutralized in a 500 ml separatory funnel with 60 ml of a 10% sodium carbonate (Na$_2$CO$_3$) solution which was covered with 20 ml of diethyl ether. After neutralization, the ether phase was separated and the water phase was extracted three times with 20 ml aliquots of ether. The combined ether extracts were dried over magnesium sulfate (MgSO$_4$), and the ether was evaporated. The resulting solid (3.3 g) was recrystallized from an ether-hexane mixture to give the desired product as a pale yellow solid (2.95 g, 12.6 mmol) in 83.4% yield. The structure of the compound, 1,3-diamino-5-pentafluorosulfanylbenzene (DASP), was confirmed by $^1$H, $^{19}$F, and $^{13}$C NMR spectroscopy, mass spectrometry, and elemental analysis.

1,3-(NH$_2$)$_2$-5-SF$_5$-C$_6$H$_3$: mp 153°–154° C.; $^1$H NMR δ 6.46 (d, J=1.7 Hz, 2H), 6.07 (t, J=1.7 Hz, 1H); $^{19}$F NMR (ab$_4$ pattern) δ$_a$ 85.2 (m), δ$_b$ 61.6 (d of m) (J$_{AB}$=149.8 Hz); $^{13}$C NMR δ C-1=C-3 147.4, C-2 103.5, C-4=C-6 103.3 (quintet, J$_{SF4-C}$=4.8 Hz), C-5 155.9 (quintet J$_{SF4-C}$=20 Hz). Mass spectrum (70 eV) m/e (rel. intensity) 234 M+ (100.0), 206 (3.9), 126 (6.8), 107 [M-SF$_5$]+ (63.5).

Anal.-Calcd. for C$_6$H$_7$F$_5$N$_2$S (234.2): C, 30.77; H, 3.01; N, 11.96; S, 13.69. Found: C, 30.73; H, 3.04; N, 11.79; S, 13.56.

Although 1,1,2-trichlorotrifluoroethane was used in this reaction other chlorinated fluorocarbons known to those skilled in the art can also be used.

Although platinum oxide was the catalyst used in this reaction, palladium on charcoal (Pd/C) may also be used.

Although diethyl ether was the solvent used to separate the diamine, any non-water soluble organic solvent known to those skilled in the art may be used.

EXAMPLE 2

A polyimide polymer was prepared by dissolving 0.1405 g (0.6 mmole) of DASP into 1.6282 g of N,N-dimethylacetamide (DMAc) in a ¼ oz. snap-cap jar. Next was added 0.2719 g (0.6 mmole) of 6FDA and the mixture was allowed to stir/react over a 23 hour period. The resulting yellow solution had an inherent viscosity (at 0.5% concentration in DMAc at 35° C.) of 0.35 dL/g indicating a high degree of polymerization. A thin film was cast from the solution and was cured to 300° C. The resulting polyimide polymer had the structural formula:

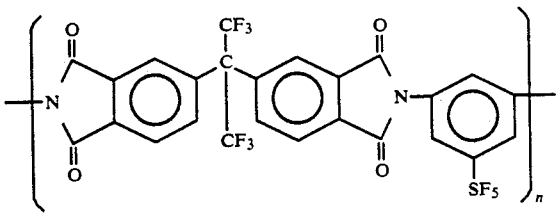

where n=10-100.

EXAMPLE 3

A polyimide polymer was prepared by dissolving 0.1124 g (0.48 mmole) DASP into 1.6563 g of DMAc in a ¼ oz. snap-cap jar. Next, 0.3017 g (0.48 mmole) of BFDA was added and the solution was allowed to stir for approximately 2 hours. An additional 0.0030 g of BFDA (1 molar percent excess) was added and the solution was stirred overnight. A pale yellow solution resulted which had an inherent viscosity of 0.44 dL/g indicating a high degree of polymerization. A thin film was cast from the solution and was cured to 300° C. The resulting polymer had the structural formula:

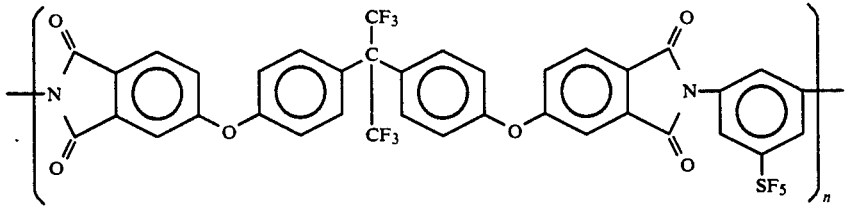

where n=10-100.

EXAMPLE 4

A polyimide polymer was prepared by dissolving 0.1850 g (0.79 mmole) DASP into 1.6698 g of DMAc in a ¼ oz. snap-cap jar. Next, 0.2348 g (0.80 mmole) of BPDA was added and the mixture was allowed to stir for approximately 24 hours. A yellow solution resulted which was found to have an inherent viscosity of 0.44 dL/g. A thin film was cast from the solution and was cured to 300° C. The resulting polymer had the structural formula:

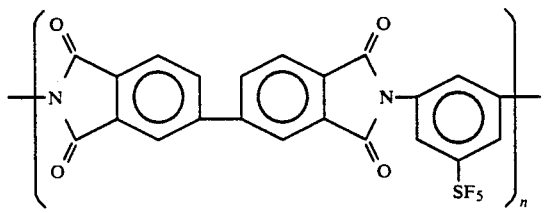

where n=10-100.

EXAMPLE 5

A polyimide polymer was prepared by dissolving 0.1756 g (0.75 mmole) DASP into 1.6332 g of DMAc in a ¼ oz. snap-cap jar. Next, 0.2350 g (0.76 mmole) of ODPA was added and the mixture was allowed to stir overnight. Another one mole percent of ODPA was added and stirring continued for approximately 4 hours. The resulting solution had an inherent viscosity of 0.48 dL/g. A thin film of this solution was cast and was cured to 300° C. The resulting polymer had the structural formula:

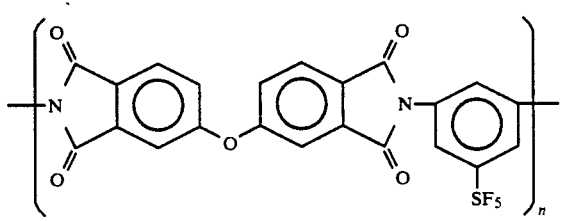

where n=10-100.

EXAMPLE 6

A polyimide polymer was prepared by dissolving 0.2108 g (0.9 mmole) of DASP into 1.6283 g of DMAc in a ¼ oz. snap-cap jar. Once the solution was attained, 0.1983 g (0.909 mmole) of PMDA was added and stirring was continued overnight. The resulting solution had a pale yellow color and an inherent viscosity of 0.36 dL/g. A thin film of this solution was cast and was cured to 300° C. The resulting polymer had the structural formula:

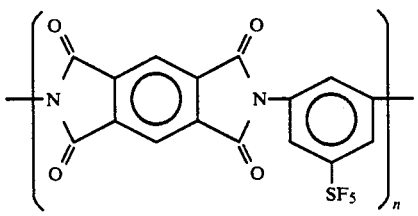

where n=10-100.

EXAMPLE 7

A polyimide polymer was prepared by dissolving 0.1710 g (0.73 mmole) of DASP into 1.6658 g of DMAc in a ¼ oz. snap-cap jar. Next, 0.2480 g (0.737 mmole) of IPAN was added and the mixture was allowed to stir. After approximately 18 hours, the viscosity appeared to be low so 0.0025 g of IPAN was added to total 0.7446 mmoles of IPAN. After stirring for approximately 4 additional hours, the polymer solution was found to have an inherent viscosity of 0.38 dL/g. A thin film of this solution was cast and was cured to 300° C. The resulting polymer had the structural formula:

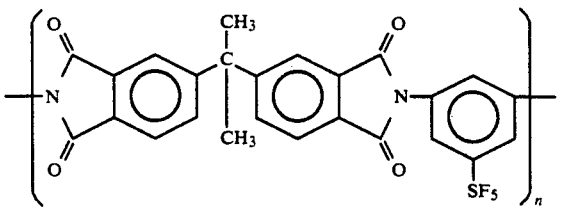

where n=10-100.

EXAMPLE 8

A polyimide polymer was prepared by dissolving 0.1733 g (0.74 mmole) of DASP into 1.647 g of DMAc in a ¼ oz. snap-cap jar. Next, 0.2408 g (0.747 mmole) of BTDA was added and the mixture was stirred overnight. The resulting solution had an inherent viscosity of 0.40 dL/g. A thin film was cast from this solution and was cured to 300° C. The resulting polymer had the structural formula:

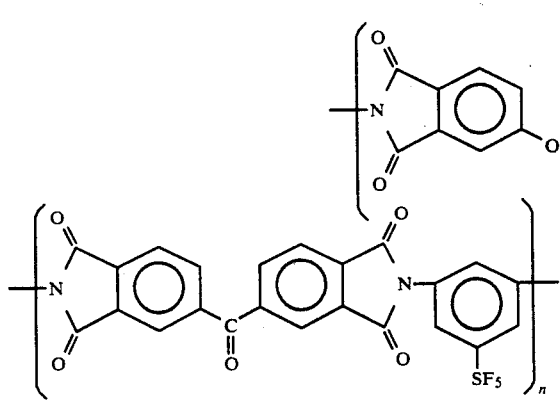

where n=10–100.

EXAMPLE 9

A polyimide polymer was prepared by dissolving 0.1499 g (0.64 mmole) of DASP into 1.6295 g of DMAc in a ¼ oz. snap-cap jar. Next, 0.2601 g (0.646 mmole) of HQDEA was added and the mixture was stirred for approximately 20 hours. The resulting pale yellow solution had an inherent viscosity of 0.40 dL/g. A thin film of this solution was cast and was cured to 300° C. The resulting polymer had the structural formula:

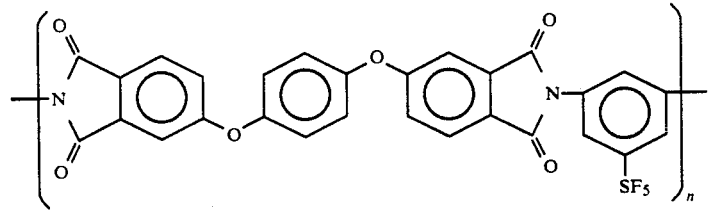

where n=10–100.

EXAMPLE 10

A polyimide polymer was prepared by dissolving 0.1288 g (0.55 mmole) of DASP into 1.6383 g of DMAc in a ¼ oz. snap-cap jar. Next, 0.2836 g (0.5555 mmole) of BDSDA was added and the mixture was allowed to stir overnight. This solution had an inherent viscosity of 0.45 dL/g. A thin film of this solution was cast and was cured to 300° C. The resulting polymer had the structural formula:

where n=10–100.

EXAMPLE 11

A semi-permeable membrane was formed from the polymer solution of Example 3. The solution was coated onto a piece of plate glass. Next, the DMAc was allowed to evaporate at room temperature for ½ hour. The remainder of the DMAc was leached from the film by immersing it in methanol to form a membrane which was subsequently thermally treated to 200° C. to form a stable polyimide semi-permeable membrane.

EXAMPLE 12

A wire coating was prepared by immersing a piece of copper wire in the polymer solution from Example 3. Upon removal from the solution, the coating was allowed to air dry for approximately ½ hour. After drying, the wire was placed in an air oven at 200° C. for one hour to cure the polyimide coating. The coating on the copper wire was flexible and resisted abrading.

Table 3 summarizes the properties of each of the aforementioned polyimide polymers.

TABLE 3

$SF_5$ Containing Polyimides

| Polyimide | Inherent Viscosity | Tg by TMA °C. | 10% Wt. Loss TGA °C. | Dielectric Constant @ 10 GHz | Film Appearance @ 1 mil |
|---|---|---|---|---|---|
| 6PDA + DASP 2% excess DA | 0.35 | 305 | 476 | 2.51 | essentially colorless |
| BPDA + DASP 1% excess DA | 0.44 | 243 | 480 | 2.61 | pale yellow to colorless |
| BPDA + DASP 1% excess DA | 0.44 | 344 | 471 | 3.00 | very pale yellow |
| ODPA + DASP 2% excess | 0.48 | 287 | 470 | 2.82 | yellow |
| PMDA + DASP | 0.36 | | ← Too Brittle → | | tiny gold flakes |
| IPAN + DASP 2% excess | 0.38 | 300 | 426 | 2.68 | pale to colorless |
| BIDA + DASP 1% excess | 0.40 | 308 | 461 | 3.00 | light yellow |
| HQDEA + DASP | 0.40 | 263 | 741 | 2.83 | very pale |

TABLE 3-continued

| | SF5 Containing Polyimides | | | | |
|---|---|---|---|---|---|
| Polyimide | Inherent Viscosity | Tg by TMA °C. | 10% Wt. Loss TGA °C. | Dielectric Constant @ 10 GHz | Film Appearance @ 1 mil |
| 1% excess BDSDA + DASP | 0.45 | 235 | 457 | 2.80 | yellow pale amber |

What is claimed as new and desired to be secured by Letters Patent of the United States is:

1. Polyimide polymers prepared from the diamine, 1,3-diamino-5-pentafluorosulfanylbenzene, having the following structural formula:

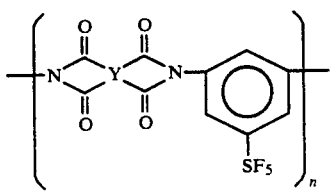

where Y is any aromatic moiety and n=10-100.

2. A polyimide polymer of claim 1, having the structural formula:

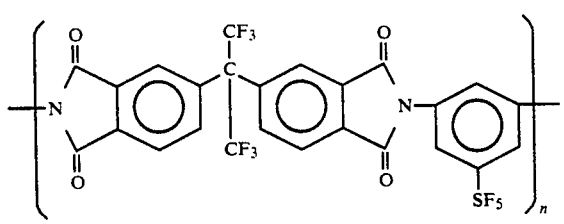

where n=10-100.

3. A polyimide polymer of claim 1, having the structural formula:

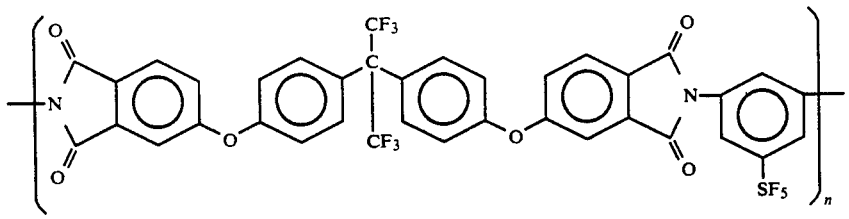

where n=10-100.

4. A polyimide polymer of claim 1, having the structural formula:

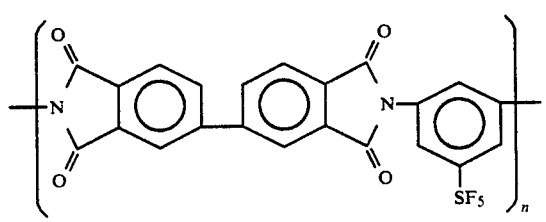

where n=10-100.

5. A polyimide polymer of claim 1, having the structural formula:

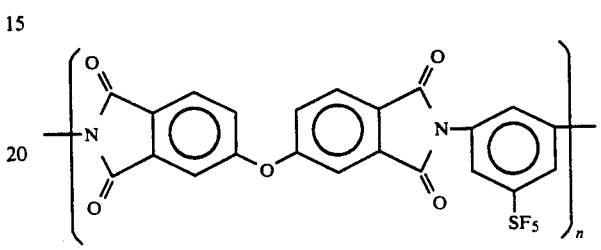

where n=10-100.

6. A polyimide polymer of claim 1, having the structural formula:

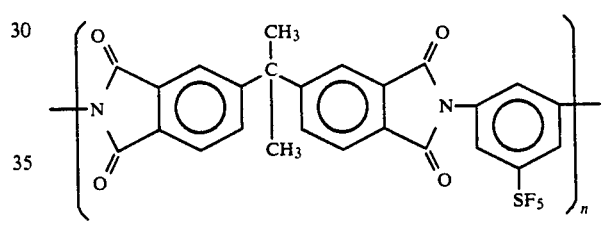

where n=10-100.

7. A polyimide polymer of claim 1, having the structural formula:

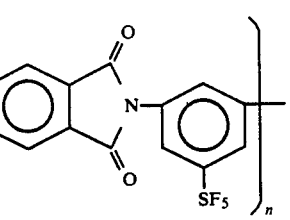

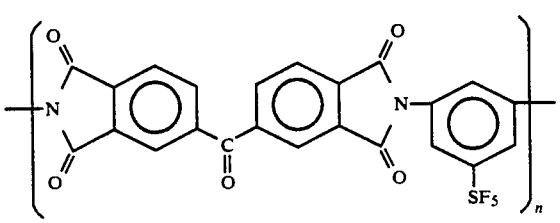

where n=10-100.

8. A polyimide polymer of claim 1, having the structural formula:

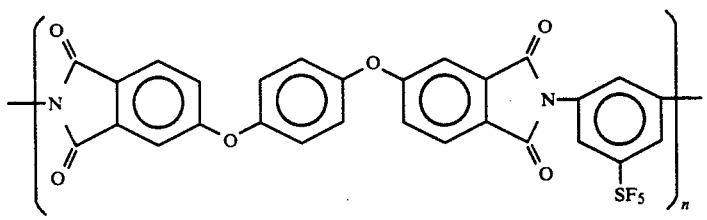
where n = 10-100.
9. A polyimide polymer of claim 1, having the structural formula:
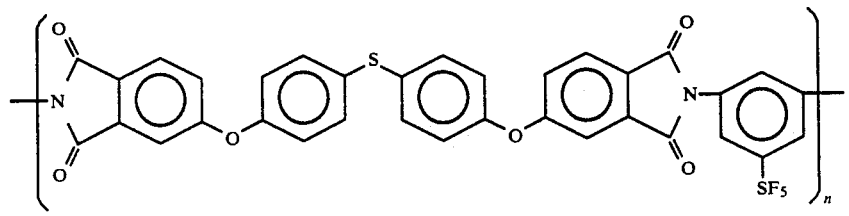
where n = 10-100.
10. Articles prepared from the polyimide polymers of claim 1, selected from the group consisting of: films, wire coating enamels, and semi-permeable membranes.
11. Articles of claim 10, wherein the article is a film.